US00PP09571P

United States Patent [19]

Endisch et al.

[11] Patent Number: Plant 9,571

[45] Date of Patent: Jun. 4, 1996

[54] GERANIUM PLANT NAMED 'RENA'

[75] Inventors: Gerd Endisch, Geranienweg, D-76767 Hagenbach; Ursula Endisch-Burmeister, Bad Kreuznach, both of Germany; Wolf Endisch, Valle Guerra/Teneriffa, Spain

[73] Assignee: Gerd Endisch, Hagenbach, Germany

[21] Appl. No.: 384,145

[22] Filed: Feb. 6, 1995

[51] Int. Cl.[6] ..... A01H 5/00

[52] U.S. Cl. ..... Plt./87.12

[58] Field of Search ..... Plt./87.12

[56] References Cited

U.S. PATENT DOCUMENTS

| | | | |
|---|---|---|---|
| P.P. 7,246 | 6/1990 | Holden | Plt./87.12 |
| P.P. 7,393 | 12/1990 | Schumann | Plt./87.12 |
| P.P. 9,151 | 5/1995 | Enthoven | Plt./87.12 |

*Primary Examiner*—James R. Feyrer

*Attorney, Agent, or Firm*—Willian Brinks Hofer Gilson & Lione

[57] ABSTRACT

A new and distinct cultivar of geranium known by the cultivar name 'Rena' is characterized by a signal red flower color, a semi-double flower form, medium green foliage, strong zonation, a compact habit and early flower response.

1 Drawing Sheet

BACKGROUND OF THE NEW PLANT

The present invention comprises a new and distinct cultivar of geranium botanically known as *Pelargonium zonale,* and hereinafter referred to by the cultivar name 'Rena'.

'Rena' is a product of planned breeding program which has the objective of creating new geranium cultivars with signal red flower color, semi-double flower form, meidum green foliage with strong zonation. Rena was originated from a hybridization made in a controlled breeding program in Hagenbach, Germany in 1990. The female parent was 'Hagenbacher Rubin', a breeding line of Geranium Endish (Hagenbach, Germany) characterized by its signal red flower color, semi-double flower form, light green foliage without zonation. 'Rena' differs from 'Hagenbacher Rubin' in that 'Rena' has shorter internodes, an earlier flower response, and leaves with stron zonation. The leaves of 'Hanenbacher Rubin' exhibit essentially no zonation. The male parent of 'Rena' was 'Bruni', a line not longer commercially available, characterized by its red flower colors, semi-double flower form, medium green foliage, medium zonation, very compact habit. 'Bruni' is more compact in growth than 'Rena' and has more petals and/or petaloids. 'Rena' also exhibits a stronger leaf zonation than 'Bruni'.

'Rena' was discovered and selected as one flowering plant within the progeny of the stated cross by the inventors in August 1991 in a controlled environment in Hagenbach, Germany.

SUMMARY DESCRIPTION OF THE NEW CULTIVAR

The first act of asexual reproduction of 'Rena' was accomplished when vegetative cuttings were taken from the initial selection in January 1992 in a controlled environment in Hagenbach, Germany, by a technician working under formuations established and supervised by Gerd Endisch.

Horticultural examination of selected units initiated in May 1992 has demonstrated that the combination of characteristics as herein disclosed for 'Rena' are firmly fixed and are retained through successive generations of asexual reproduction.

'Rena' has not been observed under all possible environmental conditions. The phenotype may vary significantly with variations in environment such as temperature, light intensity, and day length. The following observations, measurements, and comparisons describe plants grown in Hagenbach, Germany, under field conditions which approximate those generally used in commericial practice. All measurements and dimensions given below are approximate.

The following traits have been repeatedly observed and are determined to be basic characteristics of 'Rena' to distinguish this geranium as a new and distinct cultivar:

1. signal red flower color
2. semi-double flower form
3. medium green foliage
4. strong zonation
5. compact habit
6. early flower response Of the many commercial cultivars known to the present inventor, the most similar in comparison to 'Rena' is 'Grand Prix'.

Reference is made to Chart A below which compares certain characteristics of 'Rena' to those same characteristics of 'Grand Prix'. In comparison to 'Grand Prix', 'Rena' has shorter internodes, better branching pattern, more outdoor flower production, larger umbel and longer pedicel.

BRIEF DESCRIPTION OF THE DRAWINGS

The accompanying photographic drawing show typical flower and foliage characteristics of 'Rena', with colors being as true as possible with illustrations of this type.

DETAILED BOTANICAL DESCRIPTION

In the following description color references are made to *The Royal Horticultural Society Colour Chart* (R.H.S.). The color values were determined indoors from plants grown outdoors in August 1994 in Hagenbach, Germany, or Hannover (Bundessortenamt).

Classification:

*Botanical.*—A hybrid of the species *Pelargonium zonale.*

*Commercial.*—Zoanl geranium, cv. 'Rena'.

Inflorescence:

*Umbel.*—Typical umbel comprises approximately 35 flowers.

*Average diameter.*—Approx. 105–110 mm.

*Average depth.*—Approx. 54–56 mm.

*Peduncle length.*—Approx. 165–170 mm.

*Flower response.*—In Hannover, Germany, in 1993, about 50% of plants with at least one flower opened by about 13 weeks after planting of unrooted cuttings.

*Outdoor flower production.*—In Hagenbach, Germany, between May 15, 1993 and August 15, 1994 observation period, approximately 50–55 flowers per plant.

*Durability.*—Medium rain resistance.

Corolla:

*Aveage diameter.*—Approx. 46–48 mm.

*Form.*—Semi-double; cup–shaped when bloom first appears, flattening to shallow cup with maturity.

*Color.*—(General tonality form a distance of three meters) signal red.

*Petals.*—6–7 in number; 1–5 petaloids.

*Color of ;upper petals and petaloids.*—RHS 43 A/B, substanially solid signal red.

*Color of l ower petals.*—Top surface: RHS 43 A/B. Bottom surface: RHS 47D, substantially solid signal red.

*Pedicel length.*—Approx. 41–43 mm.

*Pedicel color.*—Red (anthocyanin colored).

Bud:

*Size.*—Approx. 8 mm across.

*Shape.*—Initially ovate.

*Sepals.*—Approx. 5; pointed linear lanceolate; green with red stripes.

Reproductive Organs:

*Stamens.*—Anthers: 6–7 in number. Filaments.—Approx. 5–6 cm in length. Pollen.—Orange in color.

*Pistil.*—No.: One. Length: Approx. 9 mm. Stigma: 5–6 lobes. Style: Approx. 3 mm in length; color: red.

*Ovaries.*—Green.

*Fruit.*—Partially fertile.

Plant:

*Foliage.*—Abundant quantity, leaves with strong zonation. Form: Reniform in plan. Margin: Bicrenate. Ribs and veins: Distinct venation on bottom side; not prominently different on top surface. Color (upper surface): RHS 137 B/C, strong zonation (RHS 183 B). Color (bottom surface): RHS 137 D. Textures: Leathery. Petioles: Approx. 8–9 cm in length, green.

*General appearance and form.*—bushy; compact habit. Interodne length: 18–20mm; self branching from base. Branching pattern: Good branching characteristics; 22 brances observed 15 Aug. 1994. Height: 17–19 cm from media surface. Strength: Fast rooting.

CHART A

| | New Cultivar Name: 'RENA' | Comparison Cultivar Name: 'Grand Prix' |
|---|---|---|
| Pedallabor (nottom) | RHS 470 | not known |
| Umbel diameter | 105–110 | 95–100 mm |
| depth | 54–56 | 50–52 mm |
| Pedicel length | 41–43 | 32–44 mm |
| Leaf color (top surface) | RHS 137 A/B | not known |
| Leaf zonation | RHS 183 B | not known |
| Internode length | 18–20 | 26–28 mm |
| Outdoor flower production (May 15 to Aug. 15, 1994) | 50–55 | 45–50 flowers |

What is claimed is:

1. A new and distinct cultivar of geranium plant known as 'Rena', as described and illustrated and particularly characterized by a signal red flower color, a semi-double flower form, medium green foliage, strong zonation, a compact habit and early flower response.

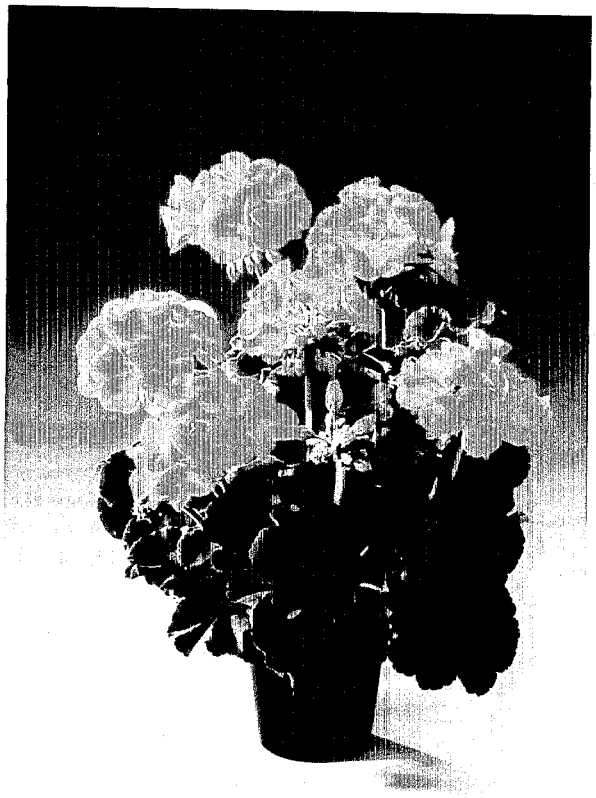

* * * * *